United States Patent [19]

Rich et al.

[11] Patent Number: 4,748,119

[45] Date of Patent: May 31, 1988

[54] PROCESS FOR ALTERING AND REGULATING GENE EXPRESSION

[76] Inventors: Alexander Rich, 2 Walnut Ave., Cambridge, Mass. 02140; Alfred E. Nordheim, 70 Revere St., Boston, Mass. 02114

[21] Appl. No.: 5,399

[22] Filed: Jan. 15, 1987

Related U.S. Application Data

[63] Continuation of Ser. No. 533,778, Sep. 19, 1983, abandoned.

[51] Int. Cl.$^4$ .................... C12N 15/00; C12P 19/34; C07H 15/12
[52] U.S. Cl. .................... 435/172.3; 435/91; 435/172.1; 935/10; 935/7; 536/27
[58] Field of Search .................... 435/172.3, 317, 91; 536/27; 530/350; 935/36, 39

[56] References Cited

PUBLICATIONS

Marx, J. L., Science, 230:794–796, 1985 (Nov.).
Lafer et al., Biochemistry, 24:5070–5076, 1985.
Nordheim et al., P.N.A.S., 79:7729–7733, 1982.
Azorin et al., Cell, 41:365–374, 1985.
Kmiec et al., Cell, 44:545–554, 1986.
Kmiec et al., Cell, 40:139–145, 1985.
Hill, BioEssays, 1984, 1(6), 244–249, as cited in Chem. Abstracts, vol. 103, p. 137233, Abstract No. 1372486.
Rich, Alexander, "Left–Handed DNA in Chemical and Biological Systems", *Structure, Dynamics, Interactions and Evolution of Biological Molecules* (Reidel Publ.), 1983, Proc., Jul. 1982, pp. 3–21.
Laimins et al., "Host–specific Activation of Transcription by Tandem Repeats from Simian Virus 40 and Moloney Murine Sarcoma Virus", *Proc. Natl. Acad. Sci.*, 79, pp. 6453–6457, Nov. 1982.
Banerji et al., "Expression of a $\beta$–Globin Gene is Enhanced by Remote SV40 DNA Sequences", *Cell*, 27, pp. 299–308 (Dec. 1981).
Benoist and Chambon, "In Vivo Sequence Requirements of the SV40 Early Promoter Region", *Nature*, 290, pp. 304–310 (Mar. 26, 1981).
Shortle et al., "Directed Mutagenesis", Ann. Rev. Genet., 1981, 15:265–94.
Wang, A. H.-J et al., Molecular Structure of a Left–Handed Double Helical DNA Fragment at Atomic Resolution, Nature, 282, 680–686 (1979).
Nordheim, A. et al, Negatively Supercoiled Plasmids Contain Left-Handed Z-DNA Segments as Detected by Specific Antibody Binding (1982), Cell, 31, 309–318.
Nordheim, A. and Rich, A., Negatively Supercoiled Simian Virus 40 DNA Contains Transcriptional Enhancer Sequences (1983), Nature, 303, 674–679.

*Primary Examiner*—Blondel Hazel
*Assistant Examiner*—Thomas D. Mays
*Attorney, Agent, or Firm*—Roman Saliwanchik; David R. Saliwanchik

[57] ABSTRACT

A process for altering the potential for Z-DNA formation which comprises altering the nucleotide sequence of DNA in vitro by site-directed mutagenesis or DNA substitution or deletion. Six rules for altering potential for Z-DNA formation are provided. These include the alternations of purine and pyrimidine residues.

13 Claims, No Drawings

PROCESS FOR ALTERING AND REGULATING GENE EXPRESSION

This application is a continuation of application Ser. No. 533,778, filed Sept. 19, 1983, now abandoned.

DESCRIPTION

BACKGROUND OF THE INVENTION

DNA is normally found as a double helix in which the Watson-Crick base pairs are held together by hydrogen bonding and the sugar-phosphate chains wind around each other in a right-handed manner. DNA directs the synthesis of proteins by serving as a template for polymerizing a strand of messenger RNA. This is accomplished by the enzyme RNA polymerase which separates the two strands of DNA and uses one of them as a template for RNA synthesis.

Recently it has been shown that the DNA double helix can exist not only in a right-handed B-DNA form but also in a somewhat less stable left-handed form, called Z-DNA due to the zig-zag organization of its sugar-phosphate chains. The base pairs in Z-DNA are "flipped over" relative to their orientation in B-DNA. This flipping process is associated with a rotation of alternate bases, usually purines, about their glycosyl bonds, so that they are in the syn conformation in Z-DNA, in contrast to the anti conformation found in B-DNA. Since purines [guanine (G) and adenine (A)] can adopt the syn conformation more easily than pyrimidines [cytosine (C) or thymine (T)], Z-DNA is favored by nucleotide sequences with alternations of pruines (Pu) and pyrimidines (Py). A number of factors determine whether Z-DNA is stable in a given piece of DNA. These factors are (1) the sequence of nucleotides, (2) the presence of negative supercoiling, (3) the binding of proteins which are specific for Z-DNA, (4) the methylation of CpG sequences at the carbon 5 position of cytosine, and (5) the presence of certain cations such as polyamines which stabilize Z-DNA.

Pertinent prior art are as follows: Structural aspects, of the left-handed Z-DNA double helix are outlined in the crystallographic study of Wang et al., Nature 282, 680–686, 1979. The identification of Z-DNA in natural DNA was first reported by Nordheim et al., Cell 31, 309-318, 1982, and the identification of Z-DNA in transcriptional enhancer segments was reported by Nordheim and Rich, Nature 303, 674-679 (1983).

BRIEF SUMMARY OF THE INVENTION

Upon modifying the regulatory elements of a gene (eukaryotic or prokaryotic) by site-directed mutagenesis, DNA substitution, or DNA deletion, there is obtained an alteration of the gene's expression. More specifically, upon modifying the potential for Z-DNA formation in genetic control regions there is obtained either an enhancement or diminution of gene expression. Whether gene expression will be enhanced or diminished will depend on the segment of the genetic control region which is modified.

Still more specifically, upon modifying DNA segments by in vitro site-directed mutagenesis or DNA deletion/substitution, in the transcription enhancer region of a eukaryotic gene, to create nucleotide sequences which have an increased potential to form Z-DNA, there is obtained an enhancement of the transcription of DNA to RNA. This enhancement is desirable for the subsequent translation of useful or significant polypeptide products, e.g., insulin, interferons, growth hormones, oncogene proteins, and the like.

Also disclosed and claimed are transcriptional enhancer DNA segments which can be inserted by known recombinant means into the genetic control regions of plasmid vectors, i.e., bacterial, viral, or from higher organisms and which can then be put into host cells and enhance the production of useful polypeptides.

Having discovered the means for enhancing gene expression, we have also found that some of these procedures when reversed, i.e., modification of a DNA segment having a potential for Z-DNA formation to have a decreased potential for Z-DNA, especially in the promoter, results in reduction of gene expression. This process of reducing gene expression by in vitro mutagenesis is useful to reduce the expression of a repressor regulatory gene, and, thus, enhance the polypeptide expression of its regulated gene.

Z-DNA segments in the promoter regions of genes affect the level of gene expression. In some genes, increasing Z-DNA potential in promoters results in a higher level of transcription.

Another method for turning a gene off was found to occur when a DNA segment in the promoter region of a gene is modified to a form which has the potential for Z-DNA formation. This is opposite to the effect found when a similar modification is made in the transcriptional enhancer region of a gene, as described above.

Genes can also be turned off by altering any dinucleotide sequence in promoter regions to the sequence CG, which can be methylated in vivo to 5 methyl C-G. This will maintain the gene in an inactive state.

DETAILED DESCRIPTION OF THE INVENTION

The expression of a gene involves the transcription of DNA to RNA, and the subsequent translation of mRNA into polypeptides. Though the expression process is complicated, it is generally recognized that the enhancement of transcription is beneficial for increased amounts of subsequent polypeptide formation.

Disclosed and claimed herein is a process for altering gene expression by modifying the transcriptional step of gene expression. This modification is made in the control region of a gene. For example, if certain modifications are made in a transcriptional enhancer region, there is obtained an enhanced transcription of DNA to RNA in neighboring genes. Such modifications vary in effectiveness in enhancing transcription. The modifications in the potential of a segment of DNA to form Z-DNA can be made by known in vitro mutagenesis procedures and are based on the following "Rules" which we have formulated:

Rule 1: In a DNA sequence with alternating purine and pyrimidine residues, the ability to form Z-DNA and stabilize it is the following: the CG sequence is greater than CA, CA is equal to TG, and both CA and TG are greater than TA.

Rule 2: Longer stretches with alternations of purines and pyrimidines yield segments which are more stable in producing Z-DNA compared with shorter sequences. The longer stretches will form Z-DNA under conditions of lower levels of negative superhelical energy.

Rule 3: Nucleotide sequences with bases out of purine/pyrimidine alternation are tolerated but the fewer the segments which are out of alternation the more Z-DNA is favored (example: the third base is out of alternation: PuPyPyPyPu).

Rule 4: CG sequences in segments containing alternating purine-pyrimidine residues can be methylated in vivo on the 5 position of cytosine, especially in the higher eukaryotes. Z-DNA formation is enhanced as a result of this chemical modification.

Rule 5: Two adjoining Z-DNA segments with alternations of purines and pyrimidines are out of phase if the segments cannot form a continuous repeat of purine/pyrimidine residues by changing one base from purine to pyrimidine (example: interruption of the phase between bases 4 and 5: PuPyPuPyPyPuPyPu). Two adjoining Z-DNA segments which are out of phase are less stable than they would be if they were both in phase, that is, if all the nucleotides were in one sequence of alternating purines and pyrimidines. However, two of these adjacent segments which are out of phase represent a greater Z-DNA potential compared with only one such segment being present. This is especially true if the segments are long.

Rule 6: Transcriptional enhancer activity is found if segments of alternating purine-pyrimidine residues exist in pairs separated by about 40 to about 80 bases. The Z-DNA flanking segments on each side of this 40- to 80-base pair spacer segment are stabilized according to the level of Z-DNA formation in each individual segment. Transcriptional enhancer activity is obtained when both Z-DNA segments are present and is much greater compared with only one being present.

Modifications of DNA sequences can be done by known in vitro site-directed mutagenic techniques. See Shortle, DiMaio and Nathans, Ann. Rev. Gen. 15, 265–294, 1981.

The determination and characterization of enhancer and promoter regions of a gene is a procedure well known in the art. See Banerji et al., Cell 27, 299–308, 1981, and Gorman et al., Molec. Cell Biol. 2, 1044–1051, 1982.

The following specific embodiments of the invention are merely illustrative of the process and products of the subject invention. These specific embodiments are based on the six rules previously disclosed. Those skilled in the art will appreciate the basic nature of this invention and can be expected to use the techniques recited herein, and obvious modifications thereof, in a manner to adapt this basic invention to individual needs. The procedures for site-directed mutagenesis, including transversions, transitions, and deletions: transformation of host cells; and all necessary assays are all well known to persons skilled in the art.

The parts of the following specific embodiments are as follows:

Part I. Modification of Nucleotide Sequences in Transcriptional Enhancer Segments to Increase or Decrease Enhancer Activity
  A. Exemplified strategy for mutational alteration of the Z-DNA potential within transcriptional enhancers.
  The examples in Part I refer to Tables I and II as indicated. These examples (1–17) illustrate the various transversions (changing a purine to a pyrimidine, or vice versa), transitions (changing of one purine for another purine, or a pyrimidine for another pyrimidine), deletions, and insertions based on the Rules disclosed above. Procedures for making these in vitro genetic alterations are well known in the art. However, Part V, infra, discloses the various procedures for further enablement.

Part II. Generation/Destruction of Enhancers by Insertion/Deletion of Entire Z-DNA Segments.

Part III. Modifying the Host Specificity of Transcriptional Enhancers.

Part IV. Modification of Transcriptional Activity by Changing Z-DNA-Forming Segments in Promoter Regions.

Part V. Methodology

Part I. Modification of Nucleotide Sequences in Transcriptional Enhancer Segments to Increase or Decrease Enhancer Activity There are two major features of transcriptional enhancers which affect their activity. First, the nucleotide sequence is of importance in those segments of DNA which form left-handed Z-DNA during transcriptional enhancer activity. It is of significance that in these segments the nucleotide sequence can be modified in such a way as to increase or decrease the ease with which these segments will form Z-DNA. Using the rules outlined above, a person skilled in the art can modify the ease or ability with which a segment of DNA will form Z-DNA. The second element in transcriptional enhancer activity relates to the sequence specificity of Z-DNA-binding proteins. It is likely that these vary among species, so that in addition to modifying the Z-forming ability of DNA segments in transcriptional enhancers, the nucleotide sequence of Z segments also can be modified in order to optimize the fit between the stabilizing Z-DNA-binding proteins and the Z-DNA segment itself.

A. Exemplified strategy for mutational alteration of the Z-DNA potential within transcriptional enhancers The pair of Z-DNA segments found in the well-known Rous sarcoma virus which are believed to provide the basis of the virus' identified transcriptional enhancer activity is used in the following examples. This enhancer consists of two segments of nucleotides containing respectively 9 and 8 base pairs :vhich can form a Z-DNA conformation. These are listed along the top of Table I where the nucleotides occupy positions 1 through 9 in the left and 1' through 8' in the right Z-DNA element. In between these is a spacer segment of 60 base pairs in length, which may vary from about 40 to about 80 base pairs in other enhancer systems. Table I lists examples of sequence modifications of this transcriptional enhancer using single base mutations. All modifications in the nucleotide sequence alter the Z-DNA-forming potential to various degrees. In Part A of Table I are described single base changes which *increase* the Z-forming potential. $Z_A$ defines the left Z-DNA segment and $Z_B$ the right Z-DNA segment.

The following Examples 1–10 refer to Part A of Table I.

EXAMPLE 1

In sequence $Z_B$ the G nucleotide in the 6' position is out of alternation with the other nucleotides. By carrying out a transversion in which G6' changes to C6' this nucleotide can be placed into alternation and thereby increase the potential of segment $Z_B$ for forming Z-DNA in accordance with Rule 3.

EXAMPLE 2

Transitions are used to modify nucleotides in producing a larger number of CG sequences. For example, changing T8 to C8 in the $Z_A$ segment results in the generation of a CG dinucleotide instead of a TG dinucleotide at positions 8 and 9. This has the effect of increasing the Z-DNA-forming potential of that section (see Rule 1) and introduction of a CG sequence also represents a new site of potential DNA methylation which in turn would stabilize the Z-DNA form even further. It should be noted that although increasing the Z-DNA-forming ability may enhance its activity as a transcriptional enhancer, it is possible that methylation may result in an extreme stabilization of Z-DNA-forming ability in this region to the point where it may even result in inactivation of transcriptional enhancement. This can be determined in a manner described below. Other transitions which could result in increased Z-DNA potential involve the removal of A6 and substitu G6, as well as substitution of G3' for A3' in $Z_B$.

EXAMPLE 3

Single base changes make it possible to increase the length of the Z-forming segment by carrying out a transversion of the nucleotides that are found flanking the potential Z-DNA segment. In segment $Z_A$, nucleotides X and Y are found at the beginning and the end of the 9-base-pair sequence, respectively. These are both pyrimidines because they represent the points at which the sequence of alternating C and G residues are terminated. However, by carrying out a transversion in which the fesidue $X_O$ is changed to a $G_O$, the sequence is now modified so that it has 9 base pairs instead of the 8 base pairs forming Z-DNA, and in accordance with Rule 2 this gives an increased potential for forming Z-DNA.

EXAMPLE 4

This involves the insertion of a residue. If, for example, a guanine residue is inserted in the position between the X0 and C1, so that it occupies the position $G_{01}$, the segment has now been lengthened to an 11-base-pair sequence of alternating purines and pyrimidines. This is due to the fact that X is a pyrimidine and insertion of a G between X and C adds two more nucleotides to the Z-DNA segment.

All of the above are examples in which modifications or insertions of single-base changes result in an increased tendency to form Z-DNA in either the nucleotide sequence $Z_A$ or $Z_B$.

It is also possible to make single-base changes which result in a *decrease* of Z-forming ability and an associated decrement in action as a transcriptional enhancer. Examples are illustrated in Table I, Part B.

EXAMPLE 5

A transversion of residue C5 to G5 is carried out. This introduces a residue which is out of alternation in the fifth position of the $Z_A$ segment

EXAMPLE 6

A transition in which residue G4 is modified to A4, thereby producing a TA dinucleotide rather than the TG dinucleotide. A modified segment $Z_A$ which forms Z-DNA less readily is the result.

EXAMPLE 7

This is a transversion of C1 to G1 in element $Z_A$, thereby reducing the length of the alternating purine/pyrimidine stretch with a concommitant decrease of Z-DNA potential.

EXAMPLE 8

A single base pair is deleted from position G8. This results in a shortening of the Z-DNA segment from 9 base pairs to 7 base pairs since position number 8 is now occupied by a pyrimidine residue rather than a purine residue.

EXAMPLE 9

By deleting residue C5, two short segments of 4 base pairs of alternating purine-pyrimidine are formed in which the likelihood of forming Z-DNA is reduced because these two segments are out of phase with each other. The resulting junction between two different Z-DNA segments would be less stable than the uninterrupted segments, in accordance with Rule 5.

EXAMPLE 10

Here a G residue is inserted between the residues in positions 4 and 5. This results in the production of two Z-DNA-forming regions, one containing 4 base pairs and one containing 6 base pairs. However, although this is a stronger Z-DNA-forming segment than the modification described in Example 9, nonetheless it has lost potential relative to the unmodified $Z_A$ sequence.

The examples described in Table I are generally indicative of the manner in which modifications of single bases using either base changes (transitions, transversions) or insertions/deletions can influence the potential for forming Z-DNA in different segments of a genome.

It is also possible to carry out a series of changes involving two bases rather than one. For technical reasons the examples which are disclosed involve two bases which are adjacent to each other. The reason for this is that the technology for making changes of two adjacent base pairs is somewhat different from that for changing two base pairs which are not adjacent.

In Part A of Table II there is disclosed examples in which two adjacent bases are modified, resulting in sequences which have a *greater* potential for forming Z-DNA.

The following Examples 11–13 refer to Part A of Table II.

EXAMPLE 11

Two transitions are made: Residue A6 is converted to G6, while residue T7 is converted to C7. This results in replacement of a CA and a TG dinucleotide by two CG dinucleotides and gives to sequence $Z_A$ a greater potential for forming Z-DNA. It also introduces two new CG sequences which can be methylated and as such can increase even further the potential for forming Z-DNA.

EXAMPLE 12

This involves one transition and one transversion. In sequence $Z_B$, residue $G_{6'}$ is changed to $C_{6'}$ and $A_{7'}$ is changed to $G_{7'}$. This results in enhancing the potential for sequence $Z_B$ to form Z-DNA by correcting the nucleotide which is out of alternation and by increasing the number of CG base pairs in the Z-forming segment.

EXAMPLE 13

This adds the insertion of a CA sequence between the 3' and 4' positions of sequence $Z_B$ which increases the total length of the Z-DNA-forming segment to 10 base pairs with 1 nucleotide out of alternation.

Part B of Table II discloses the way in which two changes in adjacent nucleotides can *decrease* the potential for forming Z-DNA.

The following Examples 14–17 refer to Part B of Table II.

EXAMPLE 14

Two transitions are put in place, one in which the residue C1 is changed to T1 and G2 is changed to A2. This produces a $Z_A$ segment with a TA dinucleotide instead of the CG sequence with a corresponding reduction in the Z-DNA-forming potential.

EXAMPLE 15

This introduces a transversion of C5 to A5; while in position 4, G4 is changed at A4. This results in a $Z_A$ sequence in which one residue is now out of alternation and a TG dinucleotide has been changed to a TA dinucleotide. This also produces a lowering in the potential for forming Z-DNA.

EXAMPLE 16

Two transversions have significantly decreased the ease with which $Z_A$ may form Z-DNA. Residue C5 is changed to A5, and residue G4 is changed to C4. This results in the introduction of two nucleotides, both of which are out of alternation, thereby producing significantly shorter segments of reduced capability to form Z-DNA on either side.

EXAMPLE 17

Residues G4 and C5 are deleted, thereby reducing the 9-base-pair segment of sequence $Z_A$ to a 7-base-pair segment which still maintains alternating purines and pyrimidines but has a significantly reduced length of Z-DNA-forming sequence.

Part II. Generation/Destruction of Enhancers by Insertion/Deletion of Entire Z-DNA Segments Larger changes can be made in nucleotide sequence which will modify the extent to which Z-DNA can be formed. For example, a transcriptional enhancer can be made by inserting into a given segment of DNA a 9-base-pair sequence such as the sequence found in segment $Z_A$ of Table I. Z-DNA segments found in a variety of enhancers vary in length from 5 to 15 base pairs. Thus, a Z-DNA segment of this size can be inserted at a given position such that it may be about 40 to about 80 base pairs removed from another Z-DNA segment which is already in the gene. This would generate the basic structural feature of a transcriptional enhancer.

Alternatively, it is possible to sharply diminish the likelihood of transcriptional enhancement by deleting an entire 5- to 15-base-pair segment which has the potential for forming Z-DNA.

Even larger changes in nucleotide sequence can be carried out through the insertion of bigger segments of Z-DNA. One can insert or delete the entire sequence of transcriptional enhancers which range in size from 50 to 150 nucleotides in length. For example, a segment of DNA has been naturally inserted into the locus of the mouse oncogene c-mos which resulted in c-mos activation. The new sequence is a Z-DNA-forming sequence of the following type: The ZA sequence GCACATGC-GCA is separated by an intervening sequence of 55 base pairs which is then followed by a second sequence ($Z_B$) of ATGTG,uns/G/ GCGCG. This entire segment of 77 nucleotides can be placed in the vicinity of the promoter of a particular gene, e.g., human growth hormone, and it would have the effect of substantially enhancing the transcriptional activity of this gene.

Since it is known that there is host specificity in enhancer sequences, it is reasonable to use Z-DNA-forming sequences from the organism in which it is desired to change the level of transcriptional activity. For example, if yeast is used, a pair of Z-DNA-forming sequences which are found in yeast can be modified using the changes that are described in Tables I and II to optimize their effectiveness as transcriptional enhancers in the same organism.

Part III. Modifying the Host Specificity of Transcriptional Enhancers

It is known that the strength of transcriptional enhancers depends to a significant degree on the specificities of the host cell. This is probably due to sequence specificities inherent in the Z-DNA-binding proteins which interact with the Z-forming regions of transcriptional enhancers. In modifying the potential of segments $Z_A$ and $Z_B$ in Tables I and II to form Z-DNA by changing the base sequence, protein binding to Z-DNA also may be affected. The extent to which the latter effect influences enhancer activity can be readily determined. Various assay systems are known which allow testing for the strength of different enhancers. These systems are listed above (Banerji et al., Cell 27, 299–308, 1981, and Gorman et al., Molec. Cell Biol. 2, 1044–1051, 1982). By performing such assays in different cell types a person skilled in the art can determine without undue experimentation how a mutational alteration of the Z-DNA potential affects the host specificity of a particular enhancer. In the example in Table I, increasing the Z-forming potential in position 3 of segment $Z_A$ by inserting a CG base pair for the AT pair may result in a significant increase of transcriptional enhancement. However, doing the same in position 7 of sequence $Z_A$ might not result in an increase in enhancer activity due to the fact that the protein itself is recognizing an AT base pair at position 7. Thus, the modifications in the Z-DNA-forming potential of the segments must be accompanied by in vivo assays in the intact cell of the particular species in which transcriptional enhancement is being enhanced or minimized. These routine tests will thus make it possible to modify the level of transcriptional enhancement tailored to the individual idiosyncrasies of the particular host cell.

Part IV. Modification of Transcriptional Activity by Changing Z-DNA-Forming Segments in Promoter Regions RNA polymerase II which transcribes the majority of all eucaryotic genes initiates its action in the immediate 5' upstream region of a gene (promoter). Promoters contain several signal sequences (i.e., CAAT-box, upstream regulatory element, Goldberg-Hogness box, etc.) which determine the rate and accurate start of transcription. The entire promoter region may involve one or several hundred nucleotides in length. Many genes have sequences in their promoter regions which have the potential for forming Z-DNA. These Z-DNAforming sequences can modify the ability of RNA polymerase to attach itself to the promoter. Thus, by altering the nucleotide sequence in the promoter region it is possible to increase or decrease the ability of Z-DNA formation and thereby modify the rate of transcription.

The methodology of site-specific mutagenesis (see below) is again employed for introduction of single or double base changes in order to modify the Z-DNA-forming potential of a promoter. The formation of strong Z-DNA-forming segments in the promoter region frequently has the effect of decreasing the extent of transcriptional activity, in contrast to transcriptional enhancers in which the ability to form Z-DNA is associated with increases in transcriptional activity. Some mutations are known in which the introduction of segments with Z-forming potential actually diminish entirely the ability to transcribe the gene. For example, in the human $\beta$ globin gene the sequence CACACCC is found. In a naturally occurring mutation the base at position $-87$ is changed from C to G so that the resultant sequence is now CACACGC. This mutant promoter does not allow $\beta$-globin production. This mutation has introduced a region of 7 base pairs with the potential for forming Z-DNA. Furthermore, it has introduced a CG sequence which is capable of methylation of cytosine in the 5 position which in turn strengthens the ability to form Z-DNA. The attachment of Z-DNA-binding proteins to this mutated segment of DNA may block the movement of RNA polymerase in the promoter region.

In in vitro experiments involving RNA polymerase III it has been observed that the failure to transcribe a *Xenopus laevis* tRNA$_{met}$f gene in a Xenopus cell-free system is associated with a sequence of 9 base pairs with a strong potential of forming Z-DNA In this case, the formation of Z-DNA is associated with inhibition of RNA polymerase III transcription. Mutational modifications which result in a decrease of Z-DNA formation (as described in the examples in Tables I and II) will result in a significant enhancement of transcriptional activity.

Frequently, gene inactivation is associated with methylation of CG sequences. This methylation is known to enhance Z-DNA-forming ability. Modification of the nucleotide sequence, as for example by using a transversion to change a CG sequence into either a TG sequence or a CA sequence, results in the loss of a methylation site, rendering a gene insensitive to inactivation through methylation. This would uncouple the gene from the methylating regulatory apparatus of the cell and thereby allow its continuous expression.

DNA in vivo is known to undergo a process known as homologous recombination, during which segments of DNA in plasmids, for example, may interchange with segments of the same or very similar DNA found in the genome. As part of our process, we introduce DNA fragments containing genes modified in their control regions, promoter or transcriptional enhancers, and have them replace the homologous genes in the genome through recombination. This allows us to substitute genes with modified potentials for expression, either increased or decreased. If dinucleotide sequences in the promoter region have substituted for them the sequences CG, these new sites can be methylated in vivo, which will result in gene inactivation. Thus the homologous gene to that introduced into the recipient cell would not be expressed if appropriately methylated.

Table III presents an example of positions at which the promoter sequence of a gene can be modified. This table lists the known nucleotide sequence of the cytochrome C gene in yeast. The amino acid sequence is given over the triplets of nucleotides which define the coding region of the gene. In addition, 240 nucleotides are listed in the 5' flanking region with the numbering starting at $-1$ immediately adjacent to the site for initiation of transcription. In this nucleotide sequence boxes have been drawn around the segments which have the potential to assume the left-handed Z-DNA conformation. In general these are long sequences with alternating purines and pyrimidines except for a few nucleotides which are out of alternation. The transcriptional activity of this gene can be modified by changing the Z-forming sequences found in this promoter. For example, the potential for forming Z-DNA can be increased by taking those residues which are out of alternation and changing them so that they are in alternation in a manner described in Tables I and II. Alternatively, the sequence can be modified to reduce the potential for forming Z-DNA as discussed in Tables I and II. In addition, larger segments of the Z-DNA-forming potential can be removed and replaced by sequences which do not have potential for forming Z-DNA. These modifications in Z-DNA-forming potential are likely to have significant effects on the ability of this gene to be transcribed in a regulated fashion. It should be emphasized that the effects of mutagenesis will be complex since several regulatory systems are impinging upon this particular promoter to regulate the level of expression. These modifications can result in both increases and decreases in expression level by affecting the potential for forming Z-DNA in different segments of the promoter. Thus, increasing the potential for forming Z-DNA in one segment may result in increased transcription, while increasing its potential in another segment may result in decreasing transcription. The actual analysis of these effects can be carried out by routine tests. The methods for modifying the Z-DNA-forming potential are described herein, but their actual effectiveness in increasing or decreasing transcriptional activity must be determined by expressing the gene in the host cell by use of standard procedures.

Part V. Methodology

The methodology which can be used in carrying out this invention, as disclosed above in the examples, is generally referred to as site-directed mutagenesis. This procedure permits changing the sequence of individual nucleotides within a given piece of DNA. This methodology has been widely developed and can be used to generate deletions, insertions, or base substitutions (transitions, transversions). A recent review by Shortle et al., supra, gives a comprehensive description and literature references of the different protocols for site-directed mutagenesis procedures. Recent advances in oligonucleotide synthesis (including the availability of DNA synthesizing machines) allow the use of synthetic oligonucleotides with predetermined base sequence in site-directed mutagenesis. Therefore, in Example 1 (Table I), where a transversion in $Z_B$ transforms residue G6' into C6, a complementary oligonucleotide sequence can be synthesized in which approximately 6 to 8 base pairs on either side of position 6' are faithfully reproduced. However, the position 6' would be occupied by a G rather than a C residue. Additionally, by using standard techniques of recombinant DNA technology, an original DNA fragment containing segment $Z_B$ can be oned into the well-known cloning vector M13 (in the following, this hybrid molecule will be referred to as M13-$Z_B$) Following this, a single-stranded form of the modified M13-$Z_B$ virus is obtained by growing it in its host organism. The 15-base-pair oligonucleotide primer is then annealed to the single-stranded version of virus M13-$Z_B$. When this annealing is carried out, double-stranded DNA is formed on either side of the modified 6' site in which there is a GG mispairing in Example 1, cited above. A complete complementary strand is then synthesized using the annealed oligonucleotide as a primer for the Klenow fragment of polymerase I. Appropriate deoxy nucleoside triphosphate substrates and T4 ligase are added so that at the end of the reaction a completely ligated circle of DNA has been prepared which is an exact copy of M13-$Z_B$ with the exception that one base in the $Z_B$ segment at position 6' has been changed to C6' instead of G6'. This material is then used to infect bacterial cells by standard prdcedures and the cells are then allowed to replicate the virus. This results in the production of two populations of M13-$Z_B$ virus one contains the original sequence with G6' (M13-$Z_B$) and the other contains the modified sequence with C6' (M13-$Z_B$1) Virus M13-$Z_B$1 is then isolated by standard techniques using hybridization with the original oligonucleotide primer as a hybridization-selection probe. Hybridization of the oligonucleotide with M13-$Z_B$ will produce a mismatch which has a lower melting temperature than the hybrid between the oligonucleotide and M13-$Z_B$1 virus, which does not have a mismatch. The resulting product has now been modified so that the transversion of Example 1 in Table I has been completed with the sequence G6' modified to C6'. This mutation will function in enhancing the Z-DNA-forming potentiality of sequence $Z_B$.

This same method can be used for transitions and transversions involving one, two, or even three nucleotides. If larger segments are used which contain areas of mismatch, then, in general, longer oligonucleotide primers are used in order to stabilize the segments which are correctly annealed.

This method also can be used for introducing deletions or insertions. In those cases, an oligonucleotide primer is synthesized by known methods for which the base to be deleted is simply omitted, and then the sequence is chosen around this deletion site which contains a large enough number of correct nucleotides so that it will anneal properly. All of the foregoing methods are well known in the art.

Some of the mutational rearrangements that are listed above involve insertion or deletion of entire segments of DNA (15 base pairs and more). Such rearrangements can be performed using the widely applied general methods of recombinant DNA technology. General steps in this technology represent restriction endonuclease fragmentation of DNA, isolation of restriction fragments, rejoining of restriction fragments by annealing with T4 DNA ligase, and transformation of bacterial and eucaryotic cells with recombinant DNA molecules. The methodology for moving pieces of DNA from one location to another are well known in the art.

Recombinant DNA methodology also can be used to insert entire Z-DNA-forming sequences near selected restriction sites. This can be carried out by using a selected set of Z-DNA poly-linkers, examples of which are shown in Table IV. Z-DNA poly-linkers are small segments of DNA which are composed of alternating purine and pyrimidine sequences. These segments contain a cluster of restriction endonuclease sites within them. The presence of the restriction endonuclease sites facilitates the ready incorporation of these segments into any segment of DNA where this restriction endonuclease site is present. For example, if the sequence GCGC, which is a substrate for the endonuclease Hha I, is present, it contains a segment with only four base pairs of alternating purine-pyrimidine sequence. However, the dodecamer poly-linker with the sequence GCGCATGCGC can be used, which contains three restriction endonuclease sites: Sbh I in the midde, flanked by Hha I on either side. Since Hha I cuts DNA with a staggered cut, leaving overhanging ends, this decamer linker can be inserted into an Hha I cleavage site. This results in elongating the DNA by 8 nucleotides and transforming a sequence GCGC into a sequence of 10 base pairs which has a strong tendency to form Z-DNA. In addition, it also has two CG sequences which can be substrate for DNA methylation.

A number of Z-DNA poly-linker segments are described in Table IV which can be used in a variety of restriction endonuclease sites. These Z-DNA polylinkers are of two types. Type A involves segments which are composed of alternating purine-pyrimidine throughout the entire oligonucleotide. Type B comprises those segments which contain alternating purinepyrimidine stretches in the center but are flanked by interchangeable sequences which have no potential to form Z-DNA. These can be placed into any site of a genome by two different methods. The genomic DNA can be cleaved by a restriction endonuclease and then that site can be blunt-ended with the single-strand specific nuclease Sl: the Z-DNA poly-linker can be attached to that site by blunt-end ligation. Alternatively, the Z-DNA-forming sequence can be flanked by non-Z-DNA-forming sequences coding for a selected restriction endonuclease cutting site. These ends can be ligated to genomic DNA which is cleaved with the same restriction endonuclease. This eliminates the need for blunt-end ligation. The use of Z-DNA poly-linkers facilitates to a considerable extent the incorporation of Z-DNA-forming elements into control regions which regulate gene expression.

TABLE I*+

Modification of Z—DNA-Forming Potential of Transcriptional Enhancers by Using Single Base Mutations

| Examples | Type of Modification | In Accordance with Z-Rule | Nucleotide Positions | | | | | | | | | | | | | | | | | | | | |
|---|---|---|---|---|---|---|---|---|---|---|---|---|---|---|---|---|---|---|---|---|---|---|---|
| | | | 0 | 1 | 2 | 3 | 4 | 5 | 6 | 7 | 8 | 9 | 10 | ...N40–80... | 1' | 2' | 3' | 4' | 5' | 6' | 7' | 8' |
| | | | X | C | G | T | G | C | A | T | G | C | Y | | A | C | A | T | G | <u>G</u> | A | T |
| | | | | | | | A. Increase Z | | | | | | | | | | | | | | | | |
| 1. | Transversion G6' to C6' | 3 | | C | G | T | G | C | A | T | G | C | | | A | C | A | T | G | C | A | T |

TABLE I* -continued
Modification of Z—DNA-Forming Potential of Transcriptional Enhancers by Using Single Base Mutations

| Examples | Type of Modification | In Accordance with Z-Rule | Nucleotide Positions 0 1 2 3 4 5 6 7 8 9 10 ... N40–80 ... 1' 2' 3' 4' 5' 6' 7' 8' |
|---|---|---|---|
| | | | X C G T G C A T G C Y            A C A T G G̲ A T |
| 2. | Transition T7 to C7 (or A6 to G6 A3' to G3') | 1 |   C G T G C A [C] G C            A C A T G G̲ A T |
| 3. | Transversion X0 to G0 | 2 | [G] C G T G C A T G C            A C A T G G̲ A T |
| 4. | Insertion Add G to 0/1 position | 2 | X [G] C G T G C A T G C Y            A C A T G G̲ A T |

B. Decrease Z

| Examples | Type of Modification | In Accordance with Z-Rule | Nucleotide Positions |
|---|---|---|---|
| 5. | Transversion C5 to G5 | 2,3 | C G T G [G] A T G C            A C A T G G̲ A T |
| 6. | Transition G4 to A4 | 1 | C G T [A] C A T G C            A C A T G G̲ A T |
| 7. | Transversion C1 to G1 | 2 | [G] G T G C A T G C            A C A T G G̲ A T |
| 8. | Deletion G8 deleted | 2 | C G T G C A T \| C Y            A C A T G G̲ A T |
| 9. | Deletion C5 deleted | 5 | C G T G \| A T G C Y            A C A T G G̲ A T |
| 10. | Insertion Add G to 4/5 position | 5 | C G T G [G] C A T G C            A C A T G G̲ A T |

*X = C or T, Y = C or T
† Underlined bases are out of purine-pyrimidine alternation.
Boxes indicate modified or added bases; vertical lines represent deleted bases.

TABLE II*†
Modification of Z—DNA-Forming Potential of Transcriptional Enhancers by Mutating Two Adjacent Bases

| Examples | Type of Modification | In Accordance with Z-Rule | Nucleotide Positions 0 1 2 3 4 5 6 7 8 9 10 ... N40–80 ... 1' 2' 3' 4' 5' 6' 7' 8' |
|---|---|---|---|
| | | | X C G T G C A T G C Y            A C A T G G̲ A T |

A. Increase Z

| 11. | Two transitions A6 to G6 T7 to C7 | 1 | C G T G C [G C] G C            A C A T G G̲ A T |
| 12. | One transition G6' to C6' One transversion A7 to G7' | 3, 1 | C G T G C A T G C            A C A T G [C G] T |
| 13. | Insertion Add (CA) to 3'-4' position | 2 | C G T G C A T G C            A C A [C A] T G G̲ A T |

B. Decrease Z

| 14. | Two transitions C1 to T1 G2 to A2 | 1 | [T A] T G C A T G C            A C A T G G̲ A T |
| 15. | One transversion C5 to A5 One transversion G4 to A4 | 3 | C G T [A A̲] A T G C            A C A T G G̲ A T |
| 16. | Two transversion C5 to A5 G4 to C4 | 3 | C G T [C A] A T G C            A C A T G G̲ A T |

TABLE II* -continued

Modification of Z—DNA-Forming Potential of Transcriptional Enhancers by Mutating Two Adjacent Bases

| Examples | Type of Modification | In Accordance with Z-Rule | Nucleotide Positions 0 1 2 3 4 5 6 7 8 9 10 ... N40-80 ... 1' 2' 3' 4' 5' 6' 7' 8' |
|---|---|---|---|
| | | | X C G T G C A T G C Y     A C A T G G̲ A T |
| 17. | Deletion G4 C5 deleted | 2 | X C G T│A T G C     A C A T G G̲ A T |

*X = C or T, Y = C or T
†Underlined bases are out of purine-pyrimidine alternation.
Boxes indicate modified or added bases; vertical lines represent deleted bases.

TABLE III

```
                                                                    XhoI
                                                              5'-CTCGAGCA
                                                              3'-GAGCTCGT
                                                                    TaqI
```

```
   FnuEI      EcoRII                          HaeIII
GATCCGCCAG │GCGTGTATATA│ GCGTGGATGGCCAGGCAACTTTAGTGCTG │ACACATACAG
CTAGGCGGTC │CGCACATATAT│ CGCACCTACCGGTCCGTTGAAATCACGAC │TGTGTATGTC
                              EcoRII
  │            │           │            │            │            │
-240         -230         -220         -210         -200         -190
```

```
                              BclI              AvaIII
GCATATATATATGTGTGCG │ACG│ ACACATGATCATATG │GCATGCATGTGC│TC│TGTATGTAT
CGTATATATATACACACGC │TGC│ TGTGTACTAGTATAC │CGTACGTACACG│AG│ACATACATA
                              FnuEI                  HgiAI
  │            │           │            │
-180         -170         -160         -140
```

```
         MboII                                                    AvaII
ATA│AAACTCTTGTTTTCTTCTTTTCTCTAAATATTCTTTCCTTATACATTA│GGTCCTTTG
TAT│TTTGAGAACAAAAGAAGAAAAGAGATTTATAAGAAAGGAATATGTAAT│CCAGGAAAC
                                                          AsuI
  │            │           │            │            │            │
-120         -110         -100         -90          -80          -70
```

```
TAGCATAAATTACTATACTTC │TATAGACACGCAAACACAAATACACACAC│ TAAATTAATA
ATCGTATTTAATGATATGAAG │ATATCTGTGCGTTTGTGTTTATGTGTGTG│ ATTTAATTAT
  │            │           │            │            │
-60          -50          -40          -30          -10
```

```
        1                        5                            10
(Met)  Thr   Glu   Phe   Lys   Ala   Gly   Ser   Ala   Lys   Lys   Gly   Ala   Thr   Leu
              EcoRI          HaeIII
ATG   ACT   GAA   TTC   AAG   GCC   GGT   TCT   GCT   AAG   AAA   GGT   GCT   ACA   CTT
TAC   TGA   CTT   AAG   TTC   CGG   CCA   AGA   CGA   TTC   TTT   CCA   CGA   TGT   GAA
                              HpaII
                │                              │                  │              │
               10                             30                 40
```

```
 15                           20                        25
Phe   Lys   Thr   Arg   Cys   Leu   Gln   Cys   His   Thr   Val   Glu   Lys   Gly   Gly
                              AccI                                                HaeIII
TTC   AAG   ACT   AGA   TGT   CTA   CAA   TGC   CAC   ACC   GTG   GAA   AAG   GGT   GGC
AAG   TTC   TGA   TCT   ACA   GAT   GTT   ACG   GTG   TGG   CAC   CTT   TTC   CCA   CCG
                                                                                  AsuI
       │                  │                  │                  │
      50                 60                 70                 80
```

```
 30                       35                        40
Pro   His   Lys   Val   Gly   Pro   Asn   Leu   His   Gly   Ile   Phe   Gly   Arg   His
                              AvaII
CCA   CAT   AAG   GTT   GGT   CCA   AAC   TTG   CAT   GGT   ATC   TTT   GGC   AGA   CAC
GGT   GTA   TTC   CAA   CCA   GGT   TTG   AAC   GTA   CCA   TAG   AAA   CCG   TCT   GTG
                              AsuI
                   │                  │                  │
                  100                110                120
```

TABLE III-continued

```
45                          50                          55
Ser  Gly  Gln  Ala  Glu   Gly  Tyr  Ser  Tyr  Thr    Asp  Ala  Asn  Ile  Lys
               AluI                                        SfaNI
TCT  GGT  ACC  GCT  GAA   GGG  TAT  TCG  TAC  ACA    GAT  GCC  AAT  ATC  AAG
AGA  CCA  GTT  CGA  CTT   CCC  ATA  AGC  ATG  TGT    CTA  CGG  TTA  TAG  TTC
          |              |                  |                  |              |
         140            150                160                170            180

60                          65                          70
Lys  Asn  Val  Leu  Trp   Asp  Glu  Asn  Asn  Met    Ser  Glu  Tyr  Leu  Thr

AAA  AAC  GTG  TTG  TGG   GAC  GAA  AAT  AAC  ATG    TCA  GAG  TAC  TTG  ACT
TTT  TTG  CAC  AAC  ACC   CTG  CTT  TTA  TTG  TAC    AGT  CTT  ATG  AAC  TGA
                    |                   |                     |              |
                   190                 200                   210            220

75                          80                          85
Asn  Pro  Lys  Lys  Tyr   Ile  Pro  Gly  Thr  Lys    Met  Ala  Phe  Gly  Gly
                              EcoRII                       HaeII
AAC  CCA  AAG  AAA  TAT   ATT  CCT  GGT  ACC  AAG    ATG  GCC  TTT  GGT  GGG
TTG  GGT  TTC  TTT  ATA   TAA  GGA  CCA  TGG  TTC    TAC  CGG  AAA  CCA  CCC
               |                    |   KpnI                       |          |
              230                  240                            250        270

90                          95                         100
Leu  Lys  Lys  Glu  Lys   Asp  Arg  Asn  Asp  Leu    Ile  Thr  Tyr  Leu  Lys
     MboII
TTG  AAG  AAG  GAA  AAA   GAC  AGA  AAC  GAC  TTA    ATT  ACC  TAC  TTG  AAA
AAC  TTC  TTC  CTT  TTT   CTG  TCT  TTG  CTG  AAT    TAA  TGG  ATG  AAC  TTT
                    |                   |                          |          |
                   280                 290                        300        310

105
Lys  Ala  Cys  Glu  Och
                                  HaeIII                       TaqI
AAA  GCC  TGT  GAG  TAA   ACAGGCCCCTTTTCCTTTGTCGATATCATGTAATTAGTTA
TTT  CGG  ACA  CTC  ATT   TGTCCGGGGAAAAGGAAACAGCTATAGTACATTAATCAAT
          |              |     AsuI     |             |            |         |
         320            330            340           350          360       370

MnlI
TGTCACGCTTACATTCACGCCCTCCCCCCACATCCGCTCTAACCGAAAAGGAAGGAGTTA
ACAGTGCGAATGTAAGTGCGGGAGGGGGGTGTAGGCGAGATTGGCTTTTCCTTCCTCAAT
          |              |             |             |            |         |
         380            390           400           410          420       430

AvaII
GACAACCTGAAGTCTAGGTCCCTATTTATTTTTTTATAGTTATGTTAGTATTAAGAACGT
CTGTTGGACTTCAGATCCAGGGATAAATAAAAAAATATCAATACAATCATAATTCTTGCA
          |         AsuI |             |             |            |         |
         440            460           470           480          490

HgaI
TATTTATATTTCAAATTTTTCTTTTTTTTC  TGTACAGACGCGTGTACGCATGTA  ACATTA
ATAAATATAAAGTTTAAAAAGAAAAAAAAG  ACATGTCTGCGCACATGCGTACAT  TGTAAT
          |              |                FnuDII           |         |
         500            510           520                 540       550

HgaI                               HindIII
TACTGAAAACCTTGCTTGAGAAGGTTTTGGGACGCTCGAAGGCTTTAATTTGCAAGCTT-3'
ATGACTTTTGGAACGAACTCTTCCAAAACCCTGCGAGCTTCCGAAATTAAACGTTCGAA-5'
          |              |             |       TaqI          |    AluI
         560            570           580                   600
```

TABLE IV

DNA Sequences Containing Multiple Restriction Endonuclease Sites Coded for by Alternating Purine-Pyrimidine Signals

```
        C  G  C  A  T  G  C  G
     G  C  G  C  A  T  G  C  G  C
  T  G  C  G  C  A  T  G  C  G  C  A
```

TABLE IV-continued

DNA Sequences Containing Multiple Restriction Endonuclease Sites Coded for by Alternating Purine-Pyrimidine Signals

```
        C  G  T  G  C  A  C  G
  C  G  C  G  T  G  C  A  C  G  C  G
```

TABLE IV-continued

DNA Sequences Containing Multiple Restriction
Endonuclease Sites Coded for by Alternating
Purine-Pyrimidine Signals

```
G G A T C C G C A T G C G G A T C C
G A A T T C G C A T G C G A A T T C
```

We claim:

1. A process for enhancing the potential for Z-DNA formation in a nucleotide sequence which comprises altering said nucleotide sequence to have alternations of purine and pyrimidine residues.

2. A process, according to claim 1, wherein said alternations of purine and pyrimidine residues are CG, CA, TG, or TA.

3. A process, according to claim 1, wherein said alternations of purine and pyrimidine residues are at least five base pairs in total length.

4. A process, according to claim 1, wherein said alternations are substantially purine and pyrimidine residues.

5. A process, according to claim 1, wherein said alternations of purine and pyrimidine residues are predominantly CG sequences.

6. A process, according to claim 1, wherein said alternations of purine and pyrimidine residues on adjoining DNA segments are out of transcriptional reading phase and said DNA segments are greater than five nucleotide bases each.

7. A process, according to claim 1, wherein said alternations of purine and pyrimidine residues exist in pairs separated by about 40 to about 80 nucleotide bases.

8. A process for diminishing the potential for Z-DNA formation in a nucleotide sequence which comprises deletion of a DNA segment which has alternations of purine and pyrimidine residues.

9. A process, according to claim 10, wherein said DNA segment is about 5 to about 15 base pairs.

10. A process, according to claim 8, which comprises deleting alternations of purine and pyrimidine residues to less than five base pairs in length.

11. A process, according to claim 8, which comprises inserting nucleotide base segments which are out of alternation with purine and pyrimidine residues.

12. A process, according to claim 8, which comprises deleting pyrimidine-purine alternations, particularly CG sequences in said nucleotide sequence.

13. A process, according to claim 8, which comprises deletion of about 40 to about 80 nucleotide bases separating pairs of alternations of purine and pyrimidine residues.

* * * * *

UNITED STATES PATENT AND TRADEMARK OFFICE
CERTIFICATE OF CORRECTION

PATENT NO. : 4,748,119

DATED : May 31, 1988

INVENTOR(S) : Alexander Rich, Alfred E. Nordheim

It is certified that error appears in the above-identified patent and that said Letters Patent are hereby corrected as shown below:

| | |
|---|---|
| Column 5: | lines 21-22: "stitu G6, as well as substitution of G3' for A3' in $Z_B$" should read --stitution by G6, as well as substitution of G3' for A3' in $Z_B$--; line 35: "fesidue" should read --residue--. |
| Column 8: | line 5: "ATCTG,uns/G/GCGCG" should read --ATGTGGGCGCG--. |
| Column 10: | line 63: "C6" should read --C6'--. |
| Column 11: | line 2: "oned" should read --cloned--. |
| Column 12: | line 39: "purinepyrimidine" should read --purine-pyrimidine--; line 46: "S1:" should read --S1;--. |
| Table III: Col. 17&18 | Triplet 47 top row: "ACC" should read --CAA--; Triplet 51 bottom row: "ATT" should read --ATA--; Triplet 71 bottom row: "CTT" should read --CTC--. |
| Claim 9: | line 1: "claim 10" should read --claim 8--. |

Signed and Sealed this

First Day of November, 1988

Attest:

DONALD J. QUIGG

Attesting Officer

Commissioner of Patents and Trademarks